(12) United States Patent
Wirth et al.

(10) Patent No.: US 6,383,816 B1
(45) Date of Patent: May 7, 2002

(54) PROBING OF SURFACE ROUGHNESS

(75) Inventors: Mary J. Wirth, Elkton, MD (US);
Cozette Cuppett, Greenwich, RI (US);
Leon Doneski, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/437,308

(22) Filed: Nov. 9, 1999

Related U.S. Application Data

(60) Provisional application No. 60/107,819, filed on Nov. 10, 1998.

(51) Int. Cl.[7] ............................................. G01N 31/00
(52) U.S. Cl. .................................... 436/5; 436/525
(58) Field of Search ................... 356/394, 109, 356/237, 385; 358/106; 435/6; 436/5, 525; 422/82; 73/104, 105

(56) References Cited

U.S. PATENT DOCUMENTS

| | | | | | |
|---|---|---|---|---|---|
| 4,222,743 A | * | 9/1980 | Wang | ........................... | 23/230 |
| 5,242,831 A | * | 9/1993 | Oki | ............................... | 436/5 |
| 5,965,446 A | * | 10/1999 | Ishikawa | ....................... | 436/5 |
| 6,094,300 A | * | 7/2000 | Kashima et al. | ............ | 359/385 |
| 6,097,484 A | * | 8/2000 | McIntosh et al. | ........ | 356/237.5 |

* cited by examiner

Primary Examiner—Jill Warden
Assistant Examiner—Samuel P Siefke
(74) Attorney, Agent, or Firm—Connolly Bove Lodge & Hutz LLP

(57) ABSTRACT

A method for assessing a surface finish on a substrate. The method applies molecules that have an interaction with the substrate to the substrate. Then illuminating the surface of the substrate and monitoring the molecules on the surface of the substrate to determine the finish of the surface of the substrate.

15 Claims, 1 Drawing Sheet

PROBING OF SURFACE ROUGHNESS

RELATED APPLICATIONS

This application is related to provisional application Ser. No. 60/107,819 filed Nov. 10, 1998 and is incorporated by reference in its entirety including the figures, for all useful purposes.

GOVERNMENT LICENSE RIGHTS

The United States Government has rights in this invention as provided for by National Science Foundation (CHE-9610446), (NSF 3-1-21-2522-05) State of Delaware Advanced Technology Center (Center for Nanomachined Surfaces) (ATC 4-2-22-3130-10).

BACKGROUND OF THE INVENTION

For many applications, the roughness features remaining on surfaces after polishing are required to be orders of magnitude smaller than the wavelength of light. It is difficult to determine in such a case when a material has been polished adequately because the present means of assessing roughness features smaller than the wavelength of light are either slow or indirect. We have invented a rapid means of detecting surface roughness features smaller than the wavelength of light.

SUMMARY OF THE INVENTION

Our invention detects roughness features rapidly by monitoring the fluorescence from molecules that adhere to roughness features. We have invented a rapid means of detecting surface roughness features smaller than the wavelength of light. The invention relates to tagging a protein with a dye, only if needed, on a substrate surface.

DETAILED DESCRIPTION OF THE INVENTION

Figure 1:
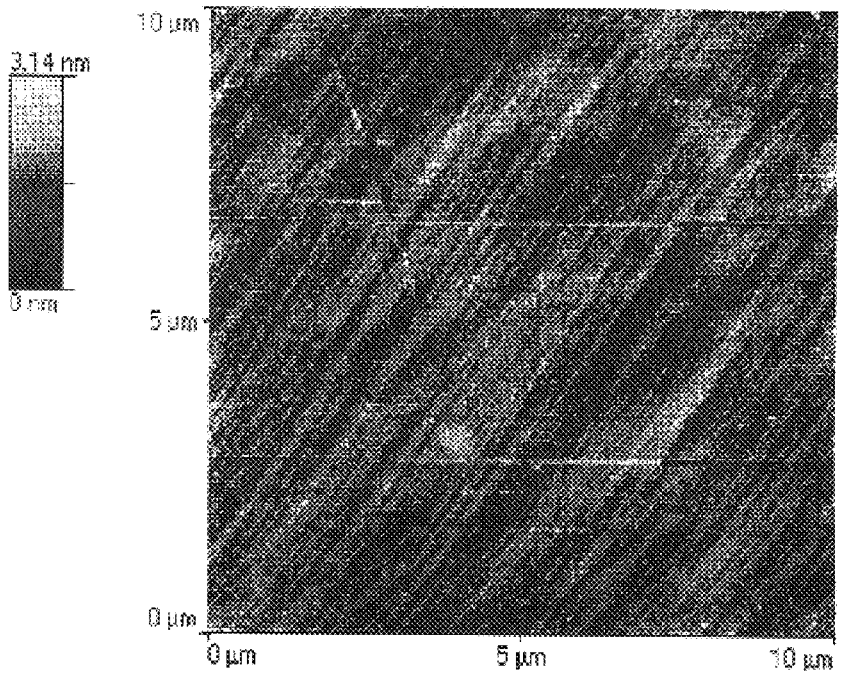
FIG. 1 illustrates an atomic force image micrograph which shows the surface topography.

The invention relates to tagging a protein with a dye only if needed on a substrate surface. Any protein or dye can be used. In our example, we used lysozyme as the protein. The dye we chose was tetramethylrhodamine. We allowed the dye-tagged protein to equilibrate with substrate surface, such as but not limited to a silica surface known to have roughness features smaller than the wavelength of light. We then rinsed the surface with pure water, illuminated the surface with 100 micro Watts of light at 514.4 nm using an air-cooled argon ion laser, and observed the fluorescence though a microscope. The images proved that the dye-tagged protein adheres to the roughness features on the surface.

The invention also works using molecules other than lysozyme, provided that they preferably have an attractive interaction with the substrate such as the silica substrate. These include most proteins, many synthetic polymers or oligomers having positive charges and/or the ability to form hydrogen-bonds, such as polyethylenimine, or smaller molecules with positive charges. Proteins, polymers and oligomers are preferred because they adhere more strongly to give better contrast, and they allow multiple tagging to make the fluorescence brighter.

A dye is needed for tagging only if the fluorescence is not easily observable. Any dye could be used for tagging, as long as its excitation spectrum matches the wavelength of the light source.

It would be possible to use a bright lamp as a light source, such as but not limited to a mercury lamp, instead of using a laser. However, a laser is preferable because it can be operated at one wavelength, simplifying the experiment. An indefinitely wide range of light powers could be used, depending on detector sensitivity, length of observation time, photobleaching rate of dye, and bandpass of filters.

It would be possible to measure optical absorbance rather than fluorescence, however, fluorescence is preferable because it provides more sensitivity. It is preferable to use dyes whose fluorescence can be excited by inexpensive lasers, including but not limited to, the fluoresceins, the rhodamines and the oxazines. We obtained images to confirm that the polishing marks are highlighted, however, the invention could be used by measuring the average fluorescence or average absorbance from the entire surface or a region of the surface, whereupon the fluorescence or absorbance would be increase with increasing surface roughness.

The method could work at any pH as long as the molecule and surface had attractive interactions at that pH. The invention was tested first with silica because it is readily available in our laboratory, but the method would work generally for surfaces. It follows that the invention would work for any oxide, including glasses and ceramics, because the adsorptive properties are similar to those of silica. The invention works for viewing roughness features on silicon, and this ability to probe a semiconductor surface indicates the invention would also work for other semiconductors, as well as metal surfaces. The method would reasonably be expected to work for plastics, such as catheters, contact lenses and other medical implants, and graphite, diamond and other elemental surface, where the roughness features would be highlighted by their stronger adsorptivities toward dyes by appropriate selection of the dye based on its charge and size.

EXAMPLES

Figure 2:
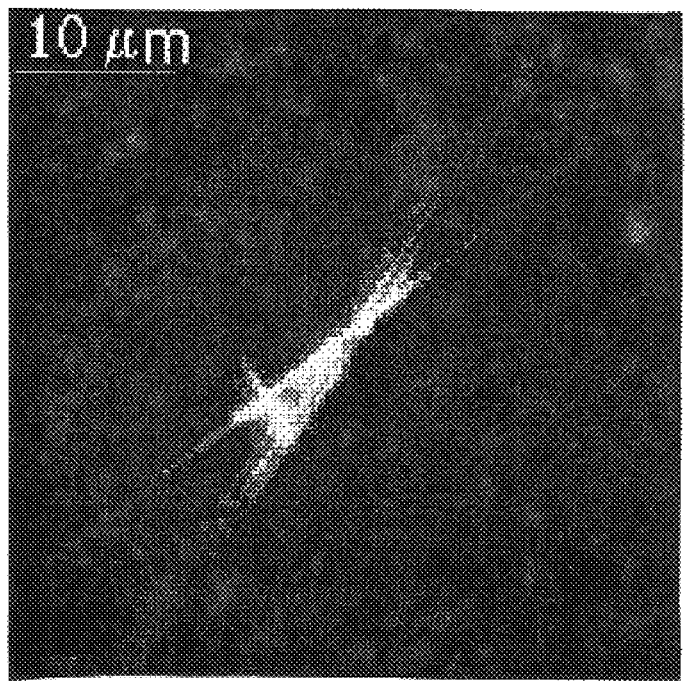
FIG. 2 illustrates a fluorescence image using a silica photomask.

Lysozyme was tagged by covalent attachment of tetramethylrhodamine using the procedure detailed by Molecular Probes, Inc., which is described in A Brief Survey of Methods for Preparing Protein Conjugates with Dyes, Haptens, and Cross-linking Agents" Michael Brinkley, *Bioconjugate Chemistry*, 1992, 3, 2–13 which is incorporated by reference, in its entirety for all useful purposes. Single-tagging was employed by control of pH, but multiple tagging is preferable because it would make the fluorescence even brighter. Silica plates were cleaned with concentrated nitric acid to remove any surface films or other chemical contaminants, and then rinsed with ultrapure water. The silica plates were then dipped into an 80 micro M aqueous solution of the tagged lysozyme at room temperature. Any concentration of lysozyme would work, but there is expected to be a longer time required as the concentration is lowered. The plates were removed and then rinsed with ultra pure water. A microscope coverslip was put on each plate and the excess water was squeezed out from between the coverslip and silica plate. Each silica plate was placed onto the sample stage of a fluorescence microscope for viewing. The beam of an argon ion laser, operated at its 514.5 nm line, was projected over a 100 $\mu$m region on the surface of the silica sample. The 514.5 line was chosen to match the excitation spectrum of tetramethylrhodamine. The resulting fluorescence from the lysozyme on the surface was viewed through the eyepieces to allow focusing on the silica surface. The surface was then translated to view various regions. The images sent with the application reveal that the fluorescence intensity highlights the polishing marks (See FIG. 2). The images were captured using a CCD camera. The surface topography was evaluated in a separate experiment using atomic force microscopy on the same silica surfaces after drying them under nitrogen (See FIG. 1). Atomic force microscopy is a standard method for evaluating surface topography, and in this case it revealed that the polishing marks are significantly smaller than the wavelength of light.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described. The examples illustrate representative products and are given by way of illustration only and are not to be considered as being limiting.

We claim:

1. A method for assessing a surface finish on a substrate which comprises applying protein molecules that have an interaction with the substrate to the substrate, illuminating the surface of the substrate and monitoring the protein molecules on the surface of the substrate to determine the finish of the surface of the substrate.

2. The method as claimed in claim 1, which further comprises tagging the molecules with a dye on the substrate surface.

3. The method as claimed in claim 2, wherein a dye-tagged protein equilibrates with the substrate surface.

4. The method as claimed in claim 1, wherein the substrate has an oxide surface.

5. The method as claimed in claim 1, wherein the substrate is an inorganic substrate.

6. The method as claimed in claim 2, wherein the substrate is silica.

7. The method as claimed in claim 1, wherein the proteins are lysozymes.

8. The method as claimed in claim 2, wherein the dye is tetramethyl-rhodamine.

9. The method as claimed in claim 1, wherein the illumination is accomplished by using a laser.

10. The method as claimed in claim 1, wherein the illumination is accomplished by using a mercury lamp or laser.

11. The method as claimed in claim 1, wherein the monitoring is accomplished by using a microscope.

12. The method as claimed in claim 1, wherein the monitoring measures optical absorbance on the surface of the substrate.

13. The method as claimed in claim 1, wherein the monitoring measures fluorescene on the surface of the substrate.

14. The method as claimed in claim 2, wherein the monitoring of molecules on the surface of the substrate is accomplished by using a microscope and measures fluorescence on the surface of the substrate and the illumination is accomplished using a laser.

15. The method as claimed in claim 14, wherein the proteins are lysozymes.

* * * * *